(12) United States Patent
Okazaki et al.

(10) Patent No.: US 10,012,611 B2
(45) Date of Patent: Jul. 3, 2018

(54) GAS SENSOR ELEMENT AND GAS SENSOR

(71) Applicant: NGK SPARK PLUG CO., LTD., Nagoya-shi, Aichi (JP)

(72) Inventors: Satoshi Okazaki, Kasugai (JP); Yuta Oishi, Aichi (JP); Seiji Oya, Aichi (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 7 days.

(21) Appl. No.: 14/603,526

(22) Filed: Jan. 23, 2015

(65) Prior Publication Data

US 2015/0212035 A1 Jul. 30, 2015

(30) Foreign Application Priority Data

Jan. 24, 2014 (JP) ................................. 2014-011383

(51) Int. Cl.
G01N 27/407 (2006.01)
G01N 27/409 (2006.01)

(52) U.S. Cl.
CPC ....... G01N 27/4071 (2013.01); G01N 27/409 (2013.01)

(58) Field of Classification Search
CPC ..................... G01N 27/409; G01N 27/4071
USPC ........... 73/31.05, 23.31–23.32; 204/424–429
See application file for complete search history.

(56) References Cited

U.S. PATENT DOCUMENTS

| 4,645,572 | A | * | 2/1987 | Nishizawa | ........... G01N 27/417 204/406 |
| 4,798,693 | A | * | 1/1989 | Mase | ................... G01N 27/417 204/425 |
| 4,875,981 | A | * | 10/1989 | Usami | ................... G01N 27/417 204/406 |
| 4,882,033 | A | * | 11/1989 | Shibata | .............. G01N 27/4065 204/425 |
| 5,174,885 | A | * | 12/1992 | Hayakawa | ........... G01N 27/417 204/424 |
| 5,236,569 | A | * | 8/1993 | Murase | ................ G01N 27/417 204/410 |
| 5,709,787 | A | * | 1/1998 | Lim | ...................... G01N 27/407 204/425 |
| 6,071,393 | A | * | 6/2000 | Oshima | ................ G01N 27/419 204/425 |

(Continued)

FOREIGN PATENT DOCUMENTS

| JP | 61-194345 A | 8/1986 |
| JP | 3-167467 A | 7/1991 |

(Continued)

OTHER PUBLICATIONS

Communication dated Jun. 6, 2017, issued by the Japanese Patent Office in corresponding Japanese application No. 2014-011383.

*Primary Examiner* — Hezron E Williams
*Assistant Examiner* — Marrit Eyassu
(74) *Attorney, Agent, or Firm* — Sughrue Mion, PLLC

(57) ABSTRACT

A gas sensor element (120) configured as a laminate of an oxygen pump cell (135) and an oxygen concentration detection cell (150) with a spacer (145) sandwiched therebetween. The spacer (145) has a gas detecting chamber (145*c*) formed therein and electrodes (138) and (152) of the cells (135) and (150), respectively, facing the chamber (145*c*). A leakage section (148) is faces the gas detecting chamber (145*c*) (measuring chamber).

6 Claims, 9 Drawing Sheets

(56) References Cited

U.S. PATENT DOCUMENTS

| | | | | |
|---|---|---|---|---|
| 6,136,170 | A * | 10/2000 | Inoue | G01N 27/4065 204/408 |
| 6,270,639 | B1 * | 8/2001 | Lenfers | G01N 27/417 204/425 |
| 6,290,840 | B1 * | 9/2001 | Kato | G01N 27/417 204/425 |
| 6,332,966 | B1 | 12/2001 | Sakai et al. | |
| 8,771,488 | B2 | 7/2014 | Ito et al. | |
| 2005/0288847 | A1 * | 12/2005 | Inoue | G01N 27/4175 701/114 |
| 2013/0032480 | A1 | 2/2013 | Ito et al. | |

FOREIGN PATENT DOCUMENTS

| | | |
|---|---|---|
| JP | 5-256817 A | 10/1993 |
| JP | 2001-13107 A | 1/2001 |
| JP | 2002-243700 A | 8/2002 |
| JP | 2013-050440 A | 3/2013 |

\* cited by examiner

GAS SENSOR ELEMENT AND GAS SENSOR

BACKGROUND OF THE INVENTION

1. Field of the Invention

The present invention relates to a gas sensor element and a gas sensor.

2. Description of the Related Art

An oxygen sensor having a pair of electrodes disposed on the outer surface of a solid electrolyte body and adapted to measure an air-fuel ratio of an internal combustion engine is known as a gas sensor for detecting a particular gas. Particularly, a laminate-type gas sensor in which two cells are laminated with a measuring chamber intervening therebetween (refer to, for example, Patent Documents 1 and 2 mentioned below) is known as a wide band gas sensor for detecting the concentration of oxygen contained in exhaust gas over a wide air-fuel ratio range of an internal combustion engine. In the laminate-type gas sensor, a first cell (also called an "oxygen concentration detection cell") outputs a voltage corresponding to oxygen concentration in the measuring chamber to an external control circuit, and a second cell (also called an "oxygen pump cell") pumps oxygen into/from the measuring chamber in accordance with current input from the control circuit.

As described in Patent Document 1, such a laminate-type gas sensor is usually driven by the control circuit, which feedback-controls current (hereinafter, also called "pump current") to be input to the oxygen pump cell, based on the output voltage of the oxygen concentration detection cell. However, in some cases, the following problem can arise in the laminate-type gas sensor: the output voltage of the oxygen concentration detection cell fails to follow a change in the pump current of the oxygen pump cell and changes with a time lag. In the case of an excessive time lag, in some cases, the control circuit can oscillate, causing fluctuations in sensor output with a resultant difficulty in stable measurement and reduced measuring accuracy.

In order to cope with the above problem, according to the technique described in Patent Document 1, the control circuit employs a high pass filter which uses a resistor and a capacitor. This configuration restrains oscillation of the control circuit as well as fluctuations in sensor output, which could otherwise result from the oxygen concentration detection cell output being greatly affected by a change in the pump current of the oxygen pump cell.

Patent Document 2 discloses a technique for restraining oscillation of the control circuit by providing a leakage section formed of zirconia between the oxygen concentration detection cell and the oxygen pump cell.

[Patent Document 1] Japanese Patent Application Laid-Open (kokai) No. 2002-243700

[Patent Document 2] Japanese Patent Application Laid-Open (kokai) No. 2013-50440

3. Problem to be Solved by the Invention

However, sufficient studies have not be conducted on the position and size of the leakage section, leaving room for improving the position and size of the leakage section for effectively restraining oscillation of the control circuit.

SUMMARY OF THE INVENTION

The present invention has been made to solve the above problems and can be embodied as follows.

A gas sensor element (1) comprising: a measuring chamber into which a gas to be measured is introduced; an oxygen concentration detection cell which generates an output voltage corresponding to oxygen concentration in the measuring chamber and which comprises a plate-shaped first solid electrolyte body and a first pair of electrodes disposed on the first solid electrolyte body, at least a portion of a first electrode of the first pair of electrodes facing the measuring chamber; an oxygen pump cell which comprises a plate-shaped second solid electrolyte body and a second pair of electrodes disposed on the second solid electrolyte body, the oxygen pump cell being laminated on the oxygen concentration detection cell with the measuring chamber intervening therebetween so that at least a portion of a second electrode of the second pair of electrodes faces the measuring chamber, and which oxygen pump cell pumps oxygen into or out of the measuring chamber in accordance with a pump current input thereto such that the output voltage generated by the oxygen concentration detection cell assumes a predetermined target voltage; an insulating layer in which the measuring chamber is formed and which is disposed between the first and second solid electrolyte bodies so as to electrically insulate the oxygen concentration detection cell from the oxygen pump cell; and a leakage section which is formed primarily of a solid electrolyte material and which electrically connects the oxygen concentration detection cell and the oxygen pump cell. Further, the leakage section faces the measuring chamber.

According to the gas sensor element (1), the leakage section is arranged so as to face the measuring chamber. Therefore, oscillation of the control circuit can be effectively restrained.

In a preferred embodiment (2), the gas sensor element above is configured as follows: when, of opposite sides of the gas sensor element with respect to an axial direction of the gas sensor element, a side where the measuring chamber is provided is defined as a forward side and a side opposite the forward side is defined as a rearward side, the leakage section includes at least one of a first leakage section which forms a wall of the measuring chamber on the forward side, and a second leakage section which forms a wall of the measuring chamber on the rearward side.

The above configuration (2) can further restrain oscillation of the control circuit.

In another preferred embodiment (3), the gas sensor element (1) or (2) above is configured such that the leakage section extends rearward beyond a rear end of each of the first and second solid electrolyte bodies. The above configuration (3) can yet even further restrain oscillation of the control circuit.

The present invention can be implemented in various forms; for example, a gas sensor element, a gas sensor comprising the gas sensor element (1) or (2) above for detecting a particular gas contained in a gas to be measured, a gas detector, and a vehicle including the gas detector mounted thereon.

DESCRIPTION OF SYMBOLS AND REFERENCE NUMERALS

Figure 1:
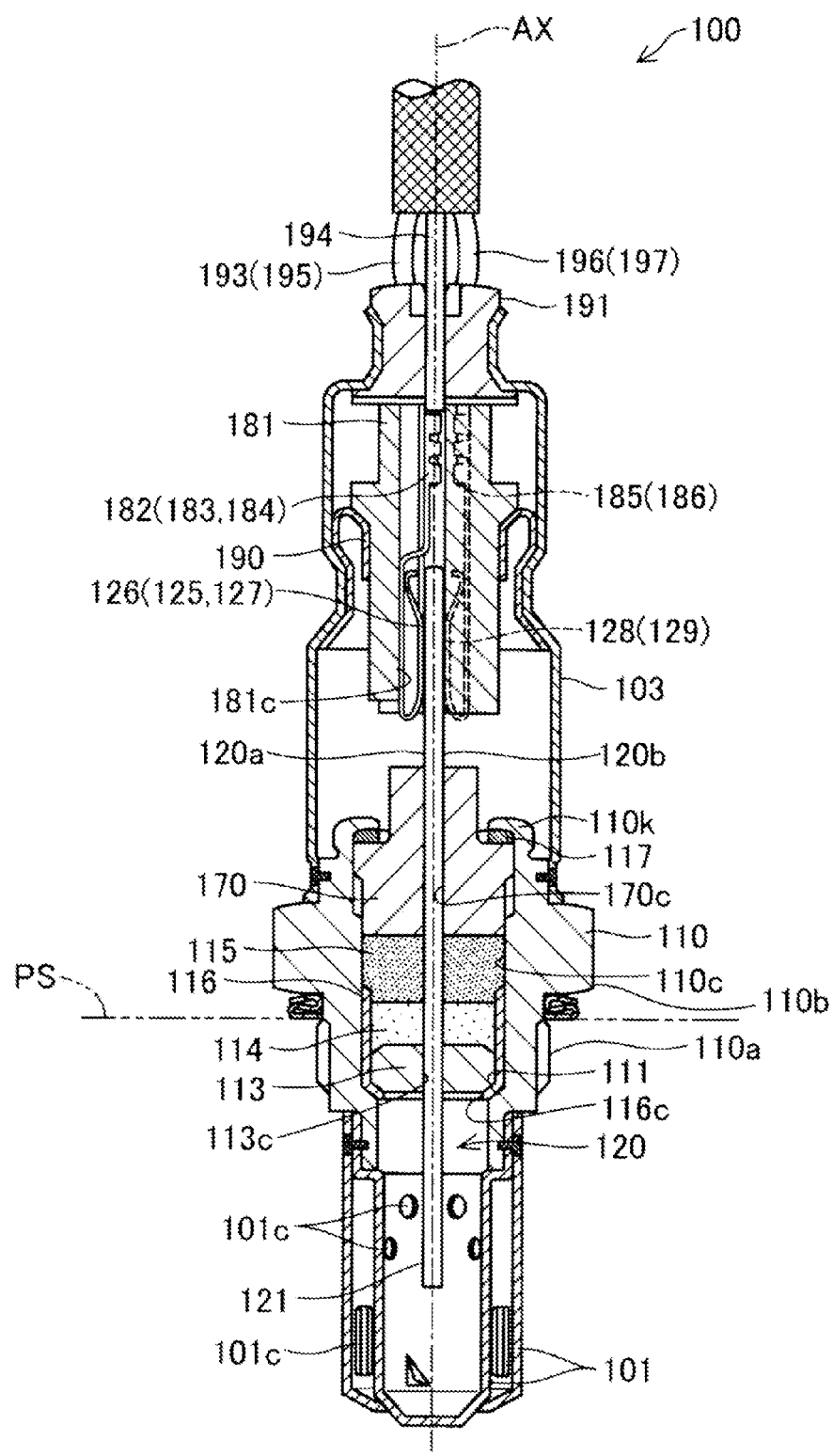
FIG. 1 is a schematic sectional view showing the internal structure of a gas sensor.

Symbols and reference numbers used to identify various features in the drawings include the following.
11-18: first to eighth through-hole conductors
21, 22: heater through-hole conductor
100, 100A, 100B, 100a: gas sensor
101: protector
101c: introduction hole
103: outer tube
110: metallic shell
110c: through hole
110k: end portion
111: stepped portion
113: ceramic holder
113c: through hole
114: first powder filler layer
115: second powder filler layer
116: metal cup
116c: through hole
117: crimp ring
120: gas sensor element
120a: first surface
120b: second surface
121: gas detecting section
125: first electrode pad (Ip electrode pad)
126: second electrode pad (COM electrode pad)
127: third electrode pad (Vs electrode pad)
128, 129: heater electrode pad
130: detection element
131: protection layer
132: porous section
135: oxygen pump cell
136: solid electrolyte body
136a, 136b: first surface, second surface
137: electrode
137L: lead portion
137M: electrode portion
138: electrode
138L: lead portion
138M: electrode portion
139: alumina layer
145: spacer
145c: gas detecting chamber
146: diffusion controlling portion
148, 148a-148d: leakage section
150: oxygen concentration detection cell
151: solid electrolyte body
151a, 151b: first surface, second surface
152: electrode
152L: lead portion
152M: electrode portion
153: electrode
153L: lead portion
153M: electrode portion
154: alumina layer
160: heater element
161, 162: first and second insulators
163: heat-generating resistor
164, 165: heater lead portion
170: ceramic sleeve
170c: axial hole
181: separator
181c: through hole
185, 186: connection terminal
190: urging metal member
191: grommet
193-197: lead wire
200, 200a: control circuit
210: PID element
211: operational amplifier
221-223: resistance
230: reference power supply
240: high-pass filter
241: resistance
242: capacitor

DETAILED DESCRIPTION OF THE PREFERRED EMBODIMENTS

FIG. 1 is a schematic sectional view showing the internal structure of a gas sensor 100 according to an embodiment of the present invention. FIG. 1 shows an imaginary center axis AX (hereinafter, also called the "axial line AX") of the gas sensor 100 with a dot-dash line. The gas sensor 100 is a so-called full range air-fuel ratio sensor which is attached to, for example, an exhaust pipe of an internal combustion engine and detects the oxygen concentration in an exhaust gas to be measured, linearly over a wide range of a rich region to a lean region.

The gas sensor 100 extends along the axial line AX. The gas sensor 100 is fixedly attached to the outer surface of the exhaust pipe such that a forward portion (a lower portion on the paper on which FIG. 1 appears) is inserted into the exhaust pipe, whereas a rear portion (an upper portion on the paper) protrudes outward from the exhaust pipe. FIG. 1 shows, with a dash-dot-dot line PS, the outer surface of the exhaust pipe on which the gas sensor 100 is attached.

The gas sensor 100 includes a metallic shell 110 adapted to fixedly attach the same to the exhaust pipe. The metallic shell 110 is a tubular metal member which has a through hole 110c extending therethrough along the axial line AX. The metallic shell 110 externally has a threaded portion 110a which is threadingly engaged with a threaded hole provided in the exhaust pipe for attaching the gas sensor 100 to the exhaust pipe, and a tool engagement portion 110b with which a tool, such as a spanner or wrench, is engaged in attaching the gas sensor 100 to the exhaust pipe.

A closed-bottomed cylindrical protector 101 having a dual structure is laser-welded to a forward end portion of the metallic shell 110. The dual-structure protector 101 has a plurality of introduction holes 101c formed in inner and outer walls thereof for allowing introduction of exhaust gas into the gas sensor 100 attached to the exhaust pipe.

An outer tube 103 formed of metal is laser-welded to a rear end portion of the metallic shell 110. Three sensor lead wires 193, 194, and 195 and two heater lead wires 196 and 197 are inserted from a rear end portion of the outer tube 103 into the gas sensor 100 for electrical connection between the gas sensor 100 and an external control circuit 200 (see FIG. 4). A grommet 191 formed of fluororubber is fitted into a rear end portion of the outer tube 103 for sealing the interior of the outer tube 103, and the five lead wires 193 to 197 are inserted into the outer tube 103 while extending through the grommet 191.

The gas sensor 100 includes a gas sensor element 120 which outputs a signal corresponding to oxygen concentration. The gas sensor element 120 has a laminate structure in which slender plate members are laminated, and has a rectangular columnar shape having a substantially rectangular section taken perpendicularly to the imaginary center axis AX (the details of which will be described below). The gas sensor element 120 is fixedly held in the through hole 110c of the metallic shell 110 and is accommodated in the gas sensor 100 along the axial line AX. In FIG. 1, first and second surfaces 120a and 120b of the gas sensor element 120 which face each other in the laminating direction are oriented leftward and rightward, respectively.

The gas sensor element 120 has a gas detecting section 121 formed at a forward end portion (a lower end portion in FIG. 1) and configured to detect oxygen concentration in exhaust gas. The gas detecting section 121 is disposed within the protector 101. Thus, the gas detecting section 121 is exposed to exhaust gas introduced through the introduction holes 101c of the gas sensor 100 attached to the exhaust pipe.

A separator 181 is a tubular insulating member which has a through hole 181c extending along the axial line AX, and is fixedly held within the outer tube 103 attached to a rear end portion (an upper end portion in FIG. 1) of the metallic shell 110. Specifically, the separator 181 is held within the outer tube 103 while being urged toward the grommet 191 by a substantially tubular urging metal member 190 disposed around the outer circumference of the separator 181. A rear end portion of the gas sensor element 120 is accommodated within the through hole 181c of the separator 181.

Three sensor electrode pads 125, 126, and 127 are arrayed on the first surface 120a of the gas sensor element 120 at a rear end portion in parallel toward the far side of the paper on which FIG. 1 appears, whereas two heater electrode pads 128 and 129 are arrayed on the second surface 120b at a rear end portion in parallel toward the far side of the paper. Furthermore, three sensor connection terminals 182, 183, and 184 and two heater connection terminals 185 and 186 are disposed within the through hole 181c of the separator 181 so as to be in contact with the corresponding electrode pads 125 to 129 of the gas sensor element 120. The sensor and heater connection terminals 182 to 186 are electrically connected to the corresponding five lead wires 193 to 197 which are inserted into the gas sensor 100 through the grommet 191.

The gas sensor element 120 is fixedly held in a tubular space of the metallic shell 110 through the following configurational features. The metallic shell 110 has a stepped portion 111 protruding radially inward into a forward end portion of the through hole 110c thereof. A metal cup 116 having a through hole 116c formed in the bottom thereof is disposed within the through hole 110c of the metallic shell 110 such that an outer circumferential portion of the bottom thereof is engaged with the stepped portion 111.

A ceramic holder 113 is disposed within the metal cup 116 and on the bottom of the metal cup 116. The ceramic holder 113 is formed of alumina ($Al_2O_3$) and has a rectangular through hole 113c formed at the center for allowing the gas sensor element 120 to extend therethrough.

A first powder filler layer 114 (talc) is formed within the metal cup 116 for airtightly holding the gas sensor element 120 which extends through the through hole 116c of the metal cup 116 and through the through hole 113c of the ceramic holder 113. The first powder filler layer 114 is formed by filling an internal space of the metal cup 116 above the ceramic holder 113 with talc powder. In this manner, the gas sensor element 120 is held in the through hole 110c of the metallic shell 110 while being integrated with the metal cup 116, the ceramic holder 113, and the first powder filler layer 114.

Furthermore, a second powder filler layer 115 (talc) is formed, through charging of talc powder, on the first powder filler layer 114 in the through hole 110c of the metallic shell 110 for securing airtightness between a rear end portion of the metallic shell 110 and the gas detecting section 121 of the gas sensor element 120. Additionally, a ceramic sleeve 170 is disposed on the second powder filler layer 115.

The ceramic sleeve 170 is a tubular member which has a rectangular axial hole 170c extending along the axial line AX for allowing the gas sensor element 120 to extend therethrough. The ceramic sleeve 170 can be formed of alumina. A rear end portion 110k of the metallic shell 110 is crimped radially inward, whereby the ceramic sleeve 170 is pressed toward the second powder filler layer 115 and fixed to the metallic shell 110. A crimp ring 117 is disposed between the ceramic sleeve 170 and the rear end portion 110k of the metallic shell 110.

Figure 2:
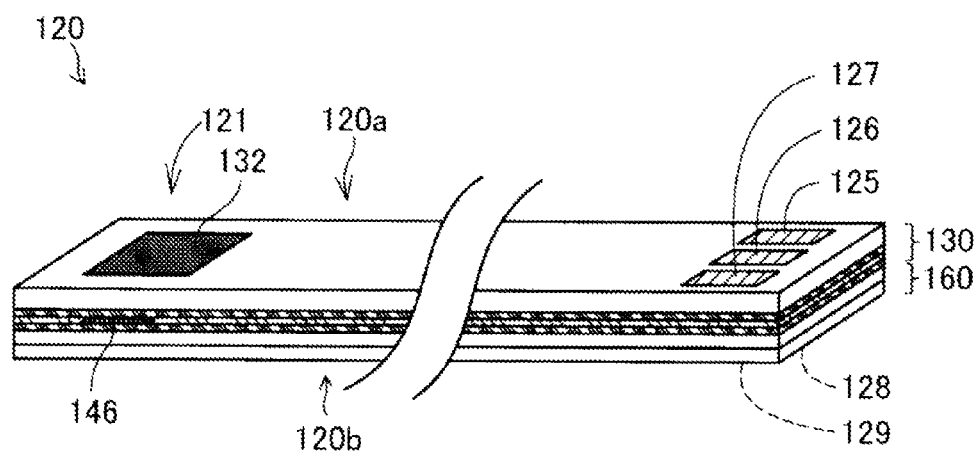
FIG. 2 is a schematic perspective view showing the configuration of a gas sensor element.

FIG. 2 is a schematic perspective view showing the configuration of the gas sensor element 120. FIG. 2 shows the gas sensor element 120 with the first surface 120a facing upward and the second surface 120b facing downward. Also, in FIG. 2, the axial line AX (FIG. 1) extends in the horizontal direction; the forward side of the gas sensor element 120 corresponds to the left side; and the rearward side corresponds to the right side. The gas sensor element 120 is configured such that a plate-shaped detecting element 130 (on the upper side in FIG. 2) and a plate-shaped heater element 160 (on the lower side in FIG. 2) are laminated and fired together.

As described with reference to FIG. 1, the gas sensor element 120 has the gas detecting section 121 formed at a forward end portion. Also, the gas sensor element 120 has the three electrode pads 125 to 127 arrayed on the first surface 120a at a rear end portion. Although unillustrated, the gas sensor element 120 has the two electrode pads 128 and 129 arrayed on the second surface 120b at a rear end portion.

Figure 3:
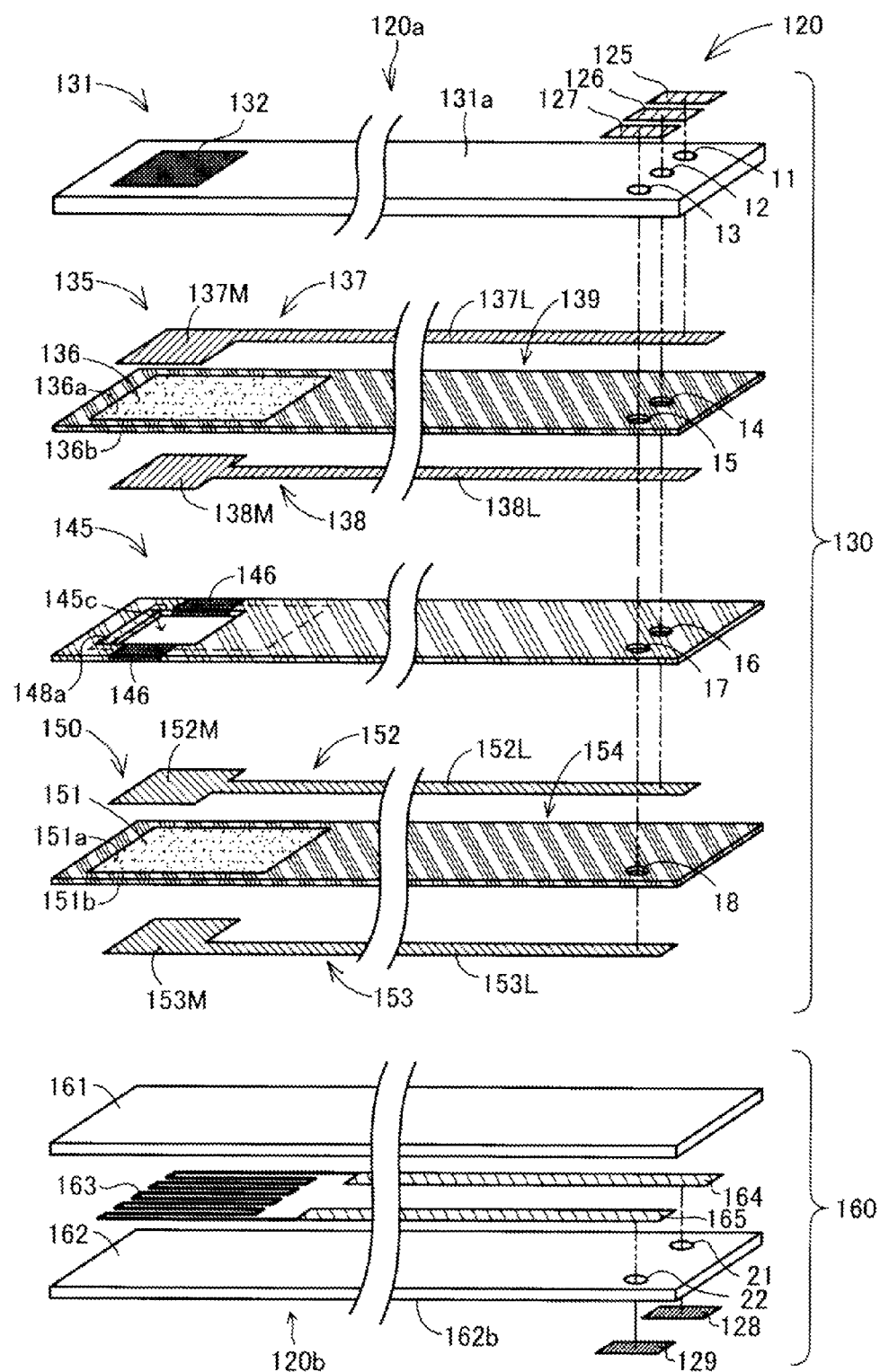
FIG. 3 is a schematic exploded perspective view showing the gas sensor element.

FIG. 3 is a schematic exploded perspective view showing the gas sensor element 120. FIG. 3 shows the components of the gas sensor element 120 separated from one another in the laminating direction (in the vertical direction in the drawing). In FIG. 3, the forward side of the gas sensor element 120 corresponds to the left side, and the rearward side corresponds to the right side. In FIG. 3, the dash-dot-dot line indicates that components connected by the dash-dot-dot line are in electrical contact with one another. In the detecting element 130 of the gas sensor 100, a protection layer 131, an oxygen pump cell 135, a spacer 145, and an oxygen concentration detection cell 150 are laminated in this order from the first surface 120a side.

The protection layer 131 is a plate-shaped member formed primarily of alumina and protects the gas sensor element 120 at the first surface 120a side. The protection layer 131 has a porous section 132 formed at a forward end portion and is gas-permeable in the laminating direction (in the vertical direction in FIG. 3). The porous section 132 is formed so as to overlie an electrode portion 137M, which will be described below, as viewed in the laminating direction of the components of the gas sensor element 120. The porous section 132 functions as a gas flow channel for exhaust gas that is pumped into or out of the gas detecting section 121.

The three electrode pads 125 to 127 are arrayed in parallel in the width direction of the gas sensor element 120 (toward the far side of the paper on which FIG. 3 appears) on an outer surface 131a of the protection layer 131 at a rear end portion. Also, the protection layer 131 has first to third through-hole conductors 11 to 13 formed therein so as to extend therethrough and which correspond to the first to third electrode pads 125 to 127.

The oxygen pump cell 135 includes a solid electrolyte body 136, an alumina layer 139 having the solid electrolyte body 136 disposed therein, and a pair of electrodes 137 and 138. The solid electrolyte body 136 is a plate-shaped member formed primarily of zirconia ($ZrO_2$) and having an area slightly greater than those of paired electrode portions 137M and 138M. The alumina layer 139 is a plate-shaped member which surrounds the outer perimeter of the solid electrolyte body 136 to perimetrically cover the solid electrolyte body 136 and which has a size substantially similar to that of the protection layer 131. The alumina layer 139 has fourth and fifth through-hole conductors 14 and 15 formed therein at a rear end portion so as to extend therethrough. The fourth and fifth through-hole conductors 14 and 15 electrically communicate with the second and third through-hole conductors 12 and 13, respectively, formed in the protection layer 131. The solid electrolyte body 136 of the oxygen pump cell 135 corresponds to the "second solid electrolyte body" of the invention.

The two electrodes 137 and 138 are formed primarily of porous platinum (Pt) and include the electrode portions 137M and 138M and lead portions 137L and 138L, respectively. The electrode portions 137M and 138M are disposed on a first surface 136a (an upper surface in FIG. 3) of the solid electrolyte body 136 and a second surface 136b (a lower surface in FIG. 3), respectively. The electrode portion 138M disposed on the second surface 136b is exposed to a gas detecting chamber 145c, which will be described below. The electrode portion 137M disposed on the first surface 136a is exposed to exhaust gas through the porous section 132 provided in the protection layer 131 when the gas sensor 100 is attached to the exhaust pipe. The electrode 138 corresponds to the "second electrode" of the invention.

The lead portions 137L and 138L extend rearward from the electrode portions 137M and 138M, respectively. The lead portion 137L of the electrode 137 disposed on the first surface 136a is in electrical contact with the first electrode pad 125 through the first through-hole conductor 11 provided in the protection layer 131. The lead portion 138L of the electrode 138 disposed on the second surface 136b is in electrical contact with the second electrode pad 126 through the fourth through-hole conductor 14 provided in the alumina layer 139 and through the second through-hole conductor 12 provided in the protection layer 131.

The spacer 145 is a plate-shaped insulating member formed primarily of alumina and having a size substantially similar to that of the alumina layer 139 of the oxygen pump cell 135. The spacer 145 has an opening portion formed at a forward end portion. The opening portion partially constitutes the gas detecting chamber 145c, into which exhaust gas to be measured is introduced, when the spacer 145 is sandwiched between the oxygen pump cell 135 and the oxygen concentration detection cell 150. The spacer 145 corresponds to the "insulating layer" of the invention, and the gas detecting chamber 145c corresponds to the "measuring chamber" of the invention.

The spacer 145 has diffusion controlling portions 146 formed at two respective side wall portions which face each other in the width direction of the spacer 145 with the opening portion intervening therebetween. The diffusion controlling portions 146 are formed of gas-permeable porous alumina. In the gas sensor element 120, exhaust gas is introduced into the gas detecting chamber 145c in an amount corresponding to the gas permeability of the diffusion controlling portions 146. That is, the diffusion controlling portions 146 function as gas introducing portions of the gas detecting section 121.

A sixth through-hole conductor 16 is formed in the spacer 145 at a rear end portion thereof and so as to extend therethrough. The sixth through-hole conductor 16 is in electrical contact with the lead portion 138L of the electrode 138 of the oxygen pump cell 135. A seventh through-hole conductor 17 is also formed in the spacer 145 adjacent to the sixth through-hole conductor 16 so as to extend therethrough. The seventh through-hole conductor 17 is in electrical contact with the fifth through-hole conductor 15 provided in the alumina layer 139 of the oxygen pump cell 135.

The spacer 145 functions as an insulating layer for electrically insulating the oxygen pump cell 135 and the oxygen concentration detection cell 150 from each other. The spacer 145 has a leakage section 148a which extends therethrough in the thickness direction of the spacer 145 and which is in electrical contact with the oxygen pump cell 135 and the oxygen concentration detection cell 150. The leakage section 148a will be described in detail below.

The oxygen concentration detection cell 150 includes a solid electrolyte body 151, an alumina layer 154 having the solid electrolyte body 151 disposed therein, and a pair of electrodes 152 and 153. The solid electrolyte body 151 is a plate-shaped member formed primarily of zirconia and having an area slightly greater than those of the paired electrode portions 152M and 153M. The alumina layer 154 is a plate-shaped member which surrounds the outer perimeter of the solid electrolyte body 151 to perimetrically cover the solid electrolyte body 151 and which has a size substantially similar to that of the spacer 145. An eighth through-hole conductor 18 formed at a rear end portion of the alumina layer 154 so as to extend therethrough. The eighth through-hole conductor 18 is in electrical contact with the seventh through-hole conductor 17 formed in the spacer 145. The solid electrolyte body 151 of the oxygen concentration detection cell 150 corresponds to the "first solid electrolyte body" of the invention.

The two electrodes 152 and 153 are formed porously and primarily of platinum (Pt) and include the electrode portions 152M and 153M and lead portions 152L and 153L, respectively. The electrode portions 152M and 153M are disposed on a first surface 151a (an upper surface in FIG. 3) of the solid electrolyte body 151 and a second surface 151b (a lower surface in FIG. 3), respectively. The electrode portion 152M disposed on the first surface 151a is exposed to the gas detecting chamber 145c. The electrode 152 corresponds to the "first electrode" of the invention.

The lead portion 152L of the electrode 152 disposed on the first surface 151a is in electrical contact with the electrode 138 of the oxygen pump cell 135 and with the second electrode pad 126 through the sixth through-hole conductor 16 provided in the spacer 145. The lead portion 153L of the electrode 153 disposed on the second surface 150b is in electrical contact with the third electrode pad 127 through the eighth through-hole conductor 18 provided in the alumina layer 154.

The heater element 160 includes first and second insulators 161 and 162, a heat-generating resistor 163, and first and second heater lead portions 164 and 165. Each of the first and second insulators 161 and 162 is a plate-shaped member formed of alumina and having the same size as the detection element 130. The first and second insulators 161 and 162 hold the heat-generating resistor 163 and the heater lead portions 164 and 165 therebetween.

The heat-generating resistor 163 is a heat-generating wire formed primarily of platinum and having a meandering shape. The two heater lead portions 164 and 165 extend rearward from respective opposite ends of the heat-generating resistor 163.

The second insulator 162 has first and second heater electrode pads 128 and 129 arrayed in parallel in the width direction of the heater element 160 on an outer surface 162b thereof at a rear end portion. Also, the second insulator 162 has first and second heater through-hole conductors 21 and 22 formed therein so as to extend therethrough. The first and second heater through-hole conductors 21 and 22 correspond to the first and second heater electrode pads 128 and 129. The first and second heater lead portions 164 and 165 extending from the heat-generating resistor 163 are in electrical contact with the first and second heater electrode pads 128 and 129 through the first and second heater through-hole conductors 21 and 22, respectively.

When the gas sensor 100 is driven, the heat output of the heater element 160 is controlled by an external heater control circuit (not shown). The heater element 160 heats the detecting element 130 to a temperature of several hundred ° C. (e.g., 700° C. to 800° C.) for activating the oxygen pump cell 135 and the oxygen concentration detection cell 150.

The leakage section 148a is formed to extend through the spacer 145 in the laminating direction so as to come into contact with the two solid electrolyte bodies 136 and 151 and with the electrodes 138 and 152 (more specifically, the lead portions 138L and 152L of the electrodes 138 and 152, respectively). Specifically, the leakage section 148a faces the gas detecting chamber 145c. In other words, the leakage section 148a is exposed to the gas detecting chamber 145c and partially constitutes the wall of the gas detecting chamber 145c. More specifically, the leakage portion 148a forms the forward wall of the gas detecting chamber 145c. Also, the leakage section 148a is formed so that the top and bottom surfaces thereof can come into contact with the corresponding cells 135 and 150 (specifically, the solid electrolyte bodies 136 and 151).

The leakage section 148a is formed primarily of a solid electrolyte material (e.g., zirconia). In the present specification, the expression "formed primarily of zirconia" means that the zirconia content of the leakage section 148a exceeds 50 wt %. More preferably, the leakage section 148a has a zirconia content of 80 wt % to 100 wt %. Preferably, in order to improve bonding with the spacer 145, the leakage section 148a contains an insulating ceramic, such as alumina, spinel, or titania ($TiO_2$), in an amount of about 0 wt % to 20 wt %.

The gas sensor 100 of the present embodiment is feedback-controlled by the control circuit 200 (which will be described below). In order to restrain the occurrence of oscillation in feedback control between the control circuit 200 and a sensor output, the leakage section 148a allows for movement of electrons and/or oxygen ions between the oxygen pump cell 135 and the oxygen concentration detection cell 150. A mechanism of the leakage section 148a in restraining oscillation during feedback control will be described in detail below.

In the gas sensor 100 of the present embodiment, in a view of the gas sensor element 120 from the laminating direction, the leakage section 148a overlies the heat-generating resistor 163 at least partially. Specifically, in projecting the leakage section 148a on the heat-generating resistor 163 along the laminating direction, at least a portion of the projected image is located on the heat-generating resistor 163. By adopting this configuration, the temperature of the leakage section 148a is controlled appropriately, whereby zirconia used to form the leakage section 148a can be maintained at an appropriate electrical conductivity. Thus, oscillation of feedback control can be reliably restrained, whereby fluctuation in the sensor output can be restrained. These features can also be applied to variants of the leakage section described below.

Preferably, in any section of the spacer 145 taken perpendicularly to the laminating direction, the area of the leakage section 148a is less than 50% of the total area of the spacer 145 and the leakage section 148a. If the leakage section 148a has the above-mentioned area percentage of 50% or greater, current (described below) which flows through the leakage section 148a becomes excessively large. That is, the spacer 145 may lose the function of an insulating layer in the gas sensor element 120, potentially resulting in deteriorating the measuring accuracy of the gas sensor 100. In this case, the area of the spacer 145 excludes the area of the opening portion which defines the gas detecting chamber 145c. In the case where two leakage sections are provided, preferably, the total area of the leakage sections satisfies the above-mentioned requirement.

Figure 4:
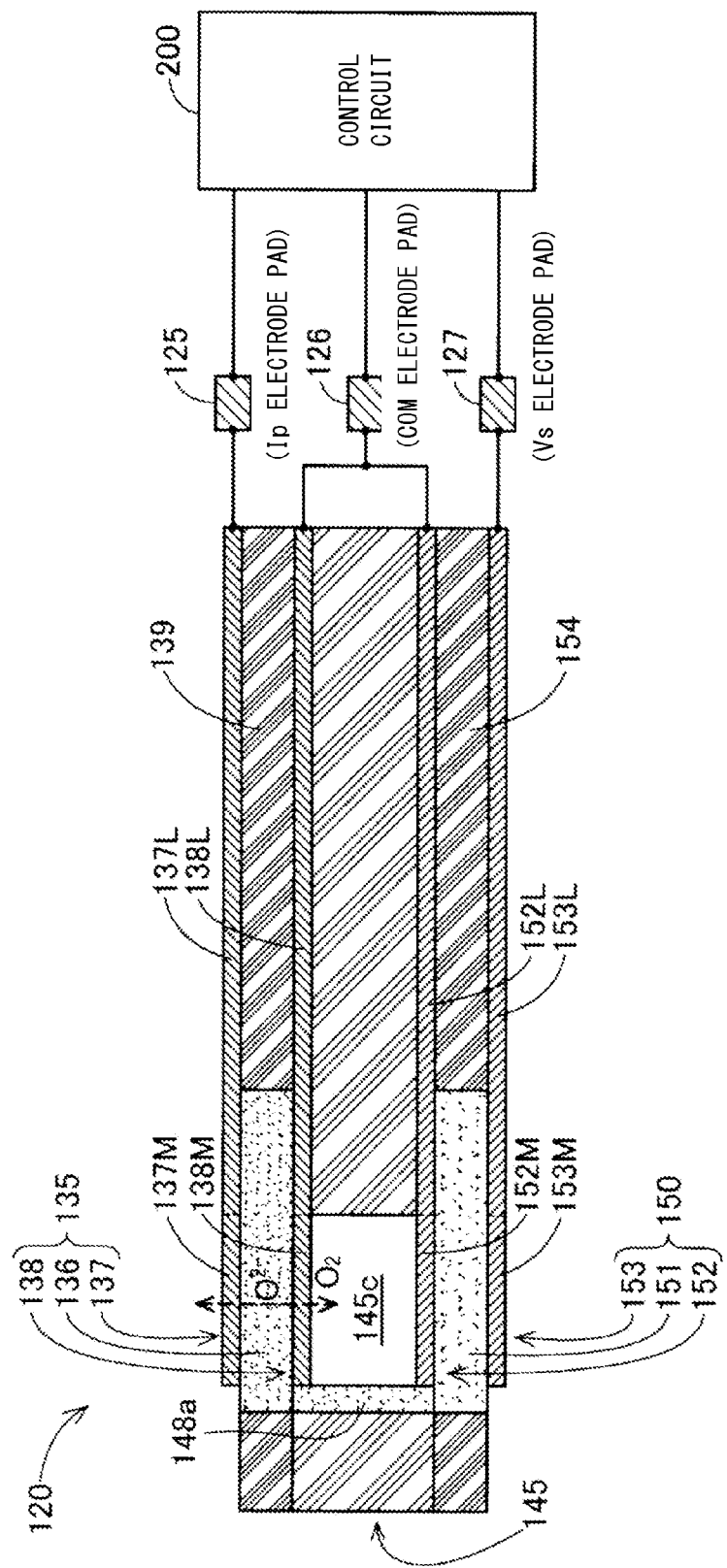
FIG. 4 is a schematic view for explaining the section of the gas sensor element and the electrical connection between the gas sensor element and a control circuit.

FIG. 4 is a schematic view which illustrates the section of the gas sensor element 120, and the electrical connection between the gas sensor element 120 and the control circuit 200. FIG. 4 schematically shows only the oxygen pump cell 135, the spacer 145, the oxygen concentration detection cell 150, and the first to third electrode pads 125 to 127 in the gas sensor element 120. FIG. 4 also shows the control circuit 200 provided externally of the gas sensor 100 and electrically connected to the oxygen pump cell 135 and to the oxygen concentration detection cell 150 through the first to third electrode pads 125 to 127.

As mentioned above, in the gas sensor element 120 of the gas sensor 100, the spacer 145 is sandwiched between the two cells 135 and 150 to thereby form the gas detecting chamber 145c within the spacer 145. The electrode portion 138M of the electrode 138 of the oxygen pump cell 135 faces the gas detecting chamber 145c and partially constitutes the wall of the gas detecting chamber 145c. As mentioned above, the leakage section 148a also partially constitutes the wall of the gas detecting chamber 145c.

Similarly, the electrode portion 152M of the electrode 152 of the oxygen concentration detection cell 150 faces the gas detecting chamber 145c and partially constitutes the wall of the gas detecting chamber 145c. Exhaust gas to be measured is introduced into the gas detecting chamber 145c through the diffusion controlling portions 146 (see FIG. 3) provided in the spacer 145.

In the solid electrolyte body 136 of the oxygen pump cell 135, when an electrical potential is generated between the electrodes 137 and 138, oxygen ions are conducted through the solid electrolyte body in the laminating direction in accordance with the magnitude and polarity of the electrical potential. In the gas sensor 100, the control circuit 200 supplies an electric current to the oxygen pump cell 135, whereby oxygen is pumped into or out of the gas detecting chamber 145c through the solid electrolyte body 136. The oxygen pump cell 135 is also called an "Ip cell."

In the solid electrolyte body 151 of the oxygen concentration detection cell 150, when a difference in oxygen concentration arises between the first surface 151a side (FIG. 3) and the second surface 151b side, an electromotive force is generated in accordance with the concentration difference. In the gas sensor 100, an electromotive force between the electrodes 152 and 153 of the oxygen concentration detection cell 150 is detected to thereby detect an oxygen concentration in the gas detecting chamber 145c based on the oxygen concentration at the electrode portion 153M of the electrode 153. The oxygen concentration detection cell 150 is also called the "electromotive force cell" or "Vs cell."

In the present specification, the first pad 125 connected to the electrode 137 of the oxygen pump cell 135 is also called the "Ip electrode pad 125." The second electrode pad 126 connected to the electrode 138 of the oxygen pump cell 135 and to the electrode 152 of the oxygen concentration detection cell 150 is also called the "COM electrode pad 126." The third electrode pad 127 connected to the electrode 153 of the oxygen concentration detection cell 150 is also called the "Vs electrode pad 127."

The control circuit 200 performs feedback control on the gas sensor element 120 as described below. The control circuit 200 detects an output voltage Vs of the oxygen concentration detection cell 150 through the COM electrode pad 126 and the Vs electrode pad 127. The control circuit 200 supplies a pump current Ip to the oxygen pump cell 135 through the Ip electrode pad 125 and the COM electrode pad 126 such that the output voltage of the oxygen concentration detection cell 150 assumes a predetermined reference value, thereby adjusting the oxygen concentration in the gas detecting chamber 145c. The control circuit 200 outputs a signal corresponding to the pump current supplied to the oxygen pump cell 135 as a signal indicative of the result of detection by the gas sensor 100.

As mentioned above, when the gas sensor 100 is driven, the electrode portion 153M of the electrode 153 of the oxygen concentration detection cell 150 functions as a closed oxygen reference chamber having a reference oxygen concentration. Thus, at startup of the gas sensor 100, the control circuit 200 supplies a very small current (e.g., about 15 µA) to the oxygen concentration detection cell 150 for introducing oxygen into the electrode portion 153M such that the oxygen concentration in the electrode portion 153M assumes a predetermined reference value.

When the gas sensor 100 is driven, the target output voltage of the oxygen concentration detection cell 150 is a voltage (e.g., about 450 mV) at which exhaust gas in the gas detecting chamber 145c has the theoretical air-fuel ratio. When the air-fuel ratio of exhaust gas in the gas detecting chamber 145c is lower than the theoretical air-fuel ratio (in a rich region), a pump current is input to the oxygen pump cell 135 in such a direction as to pump oxygen into the gas detecting chamber 145c. When the air-fuel ratio of exhaust gas in the gas detecting chamber 145c is higher than the theoretical air-fuel ratio (in a lean region), a pump current is input to the oxygen pump cell 135 in such a direction as to pump oxygen out of the gas detecting chamber 145c.

Figure 5:
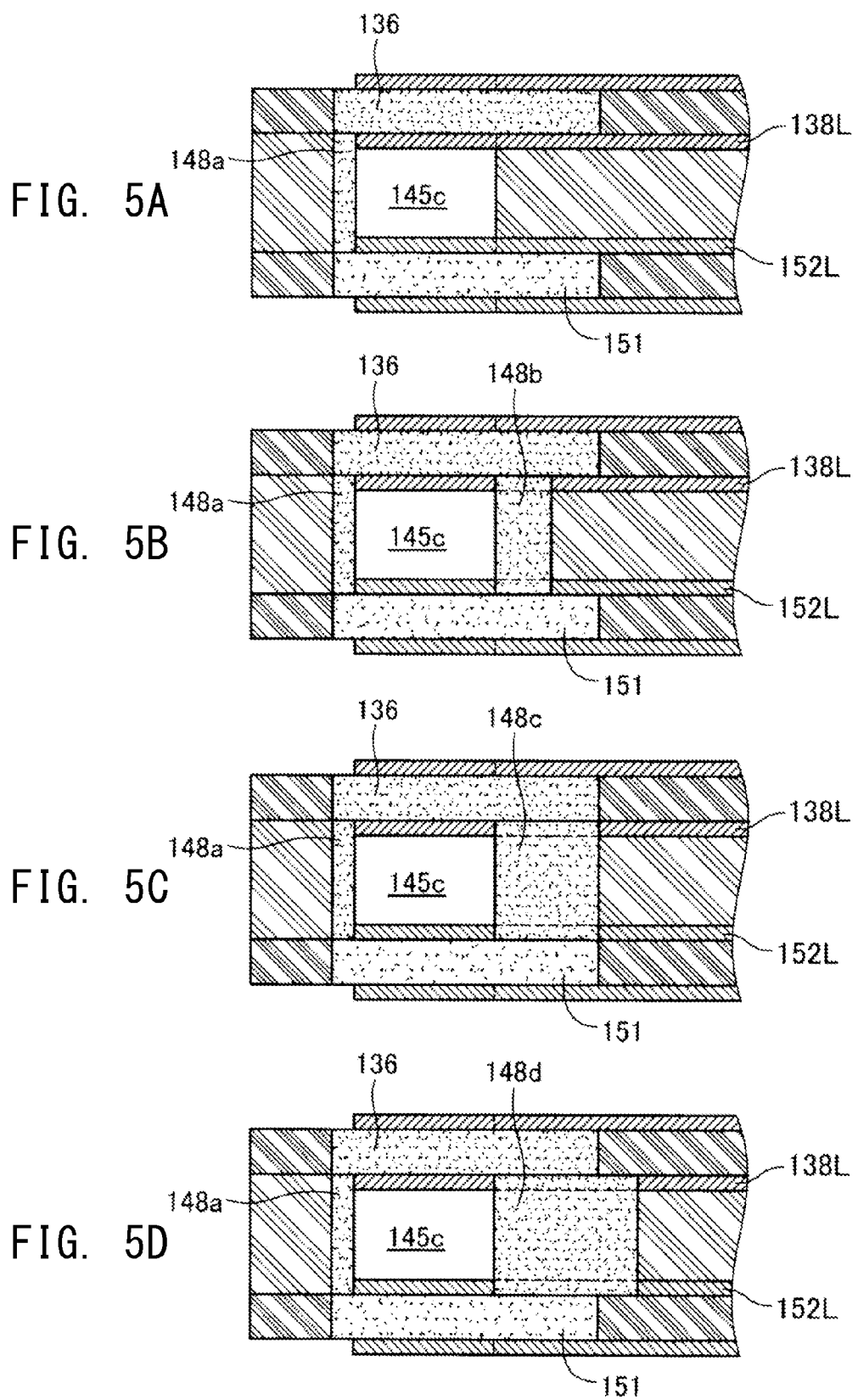
FIGS. 5A to 5D are explanatory views showing example arrangements of leakage sections.

FIGS. 5A to 5D are explanatory views showing example arrangements of leakage sections. In FIG. 5A, the leakage section 148a forms the forward (leftward in the drawing) wall of the gas detecting chamber 145c. This configuration is the same as that having been described with reference to FIGS. 3 and 4. The leakage section 148a is also called the "first leakage section 148a." In FIGS. 5B to 5D, second leakage sections 148b, 148c, and 148d are added respectively to the first leakage section 148a. Each of the second leakage sections 148b, 148c, and 148d forms the rearward (rightward in the drawing) wall of the gas detecting chamber 145c. Also, similar to the case of the first leakage section 148a, the second leakage sections 148b, 148c, and 148d are provided in direct contact with the two solid electrolyte bodies 136 and 151 and with the lead portions 138L and 152L of the two electrodes 138 and 152. The second leakage sections 148b, 148c, and 148d in FIGS. 5B to 5D differ in length along the axial direction. Specifically, the second leakage section 148b in FIG. 5B extends up to an intermediate position between the wall surface of the gas detecting chamber 145c and the rear ends (right ends in the drawing) of the two solid electrolyte bodies 136 and 151. The second leakage section 148c in FIG. 5C extends up to the rear ends of the two solid electrolyte bodies 136 and 151. The second leakage section 148d in FIG. 5D extends rearward beyond the rear ends of the two solid electrolyte bodies 136 and 151.

Figure 6:
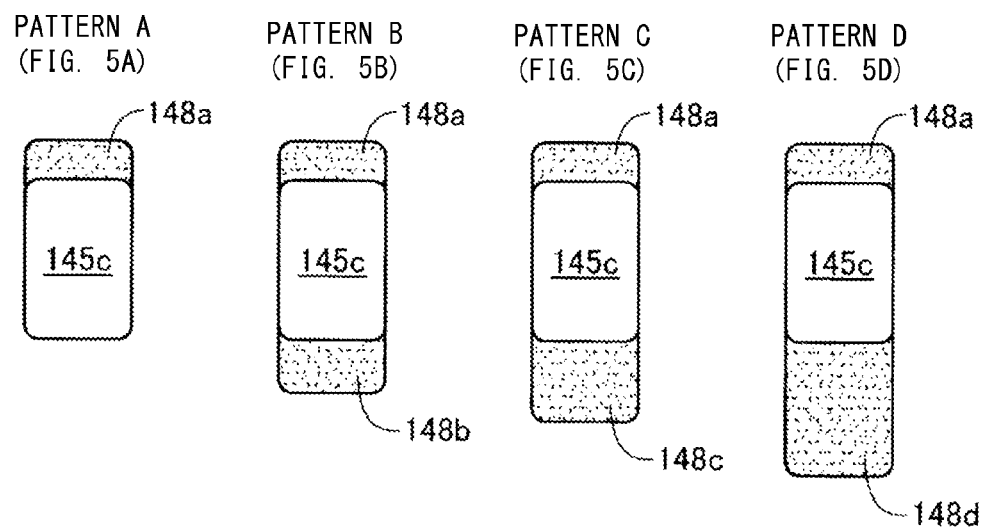
FIG. 6 is an explanatory view showing planar arrangements of leakage sections.

FIG. 6 is an explanatory view showing planar shapes of the leakage sections 148a, 148b, 148c, and 148d shown in FIGS. 5A to 5D. Hereinafter, the arrangements of the leakage sections in FIGS. 5A to 5D are called "pattern A," "pattern B," "pattern C," and "pattern D." If there is no need to distinguish the leakage sections 148a, 148b, 148c, and 148d from one another, these leakage sections are collectively called the "leakage section 148."

Incidentally, it may be the case that only the second leakage section 148b (148c, 148d) which forms the rearward wall of the gas detecting chamber 145c is provided without a first leakage section 148a which forms the forward wall of the gas detecting chamber 145c. That is, the leakage section 148 may include at least either one of the first leakage section 148a and the second leakage section 148b (148c, 148d). One of the above-mentioned arrangement patterns of the first leakage section 148a and the second leakage sections 148b, 148c, and 148d can be selected so as to produce a higher oscillation restraining effect in relation to performance of the gas sensor element 120.

Figure 7:
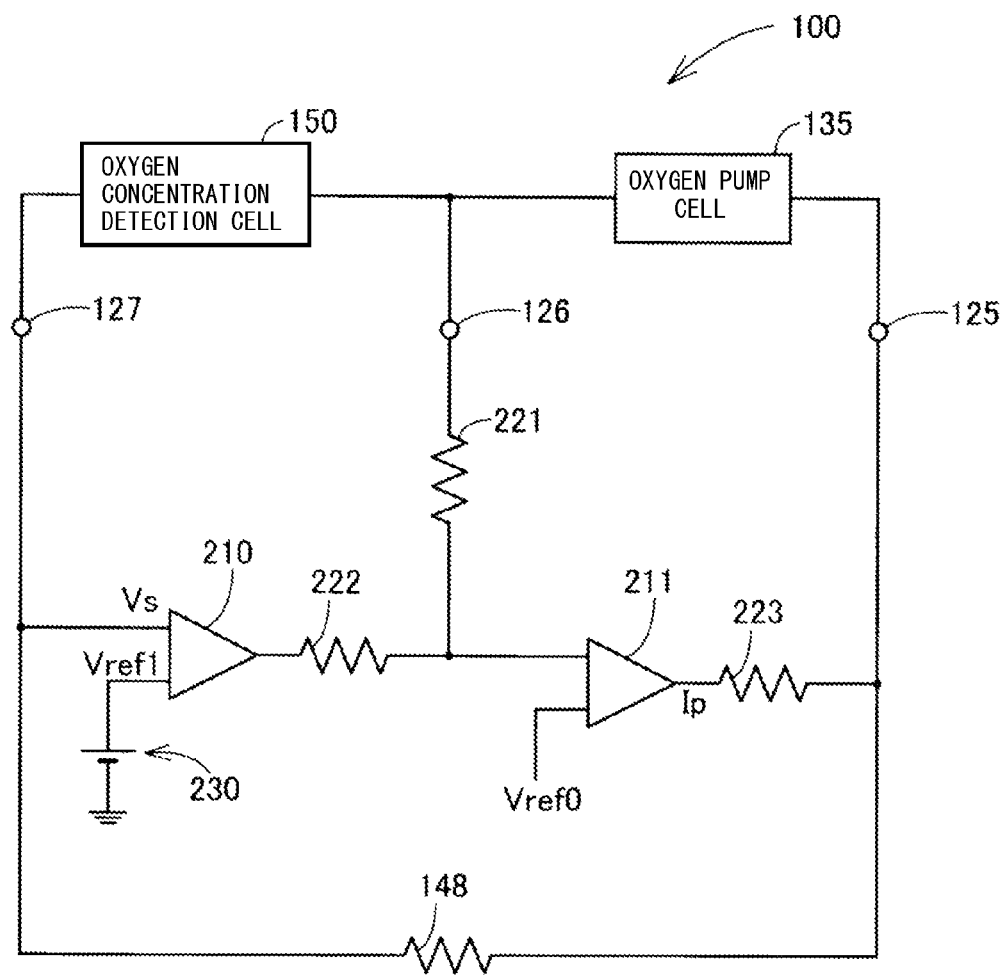
FIG. 7 is a schematic diagram showing an example configuration of the control circuit for the gas sensor.

FIG. 7 is a schematic diagram showing an example configuration of the control circuit 200 for the gas sensor 100. The control circuit 200 includes a PID (proportional, integral, and differential) element 210, an operational amplifier 211, first to third resistances 221 to 223, and a reference power supply 230. One of two input terminals of the PID element 210 is connected to the Vs electrode pad 127, whereas the other input terminal is connected to the reference power supply 230. The output terminal of the PID element 210 is connected to the COM electrode pad 126 through the first and second resistances 221 and 222 and to one of two input terminals of the operational amplifier 211 through the second resistor 222.

As mentioned above, the COM electrode pad 126 and the PID element 210 are connected to one of two input terminals of the operational amplifier 211 through the first and second resistances 221 and 222, respectively, and a reference voltage Vref0 is applied to the other input terminal. The output terminal of the operational amplifier 211 is connected to the Ip electrode pad 125 through the third resistor 223.

In this control circuit 200, the PID element 210 outputs to the operational amplifier 211 a signal corresponding to the difference between a reference voltage Vref1 output from the reference power supply 230 and the voltage Vs output from the oxygen concentration detection cell 150. The operational amplifier 211 inputs to the oxygen pump cell 135 a pump current corresponding to an output signal from the PID element 210.

Incidentally, in a conventional laminate-type gas sensor in which the oxygen pump cell and the oxygen concentration detection cell are laminated as in the case of the gas sensor 100 of the present embodiment, in some cases, when the control circuit performs feedback control as mentioned above, oscillation has occurred in the control circuit. The reason for occurrence of the oscillation is described below.

In some cases, the laminate-type gas sensor has a time lag until the output voltage of the oxygen concentration detection cell changes to a target value after the oxygen pump cell pumps oxygen into or out of the gas detecting chamber such that the output voltage of the oxygen concentration detection cell assumes the target value. This is because it takes time for oxygen molecules to move between the oxygen pump cell and the oxygen concentration detection cell in the gas detecting chamber.

Upon occurrence of such a time lag, before the voltage of the oxygen concentration detection cell reaches a target value, the pump current of the oxygen pump cell changes based on the voltage of the oxygen concentration detection cell which has not yet changed to the target value. Therefore, when the time lag becomes excessively large, the output voltage of the oxygen concentration detection cell fails to converge, causing the occurrence of oscillation in the control circuit.

By contrast, in the gas sensor 100 of the present embodiment, the leakage section 148 is provided between the oxygen pump cell 135 and the oxygen concentration detection cell 150. The leakage section 148 allows electrical communication between the two cells 135 and 150, thereby restraining the occurrence of such a time lag. Specifically, the occurrence of a time lag is restrained as described below.

Suppose that the air-fuel ratio of exhaust gas in the gas detecting chamber 145c is lower than the theoretical air-fuel ratio. At this time, the oxygen pump cell 135 pumps oxygen into the gas detecting chamber 145c. However, the electrode 152 of the oxygen concentration detection cell 150 remains low in oxygen concentration until pumped-in oxygen reaches the electrode 152.

However, in the gas sensor 100 of the present embodiment, when the pump current Ip changes, an electrical transaction occurs between the outer electrode 137 of the oxygen pump cell 135 and the electrode 152, located toward the gas detecting chamber 145c, of the oxygen concentration detection cell 150 through the leakage section 148. Specifically, when the pump current Ip changes, a portion of the pump current Ip flows (leaks) into the oxygen concentration detection cell 150 through the leakage section 148, whereby the output voltage Vs of the oxygen concentration detection cell 150 changes so as to approach a target value.

In this manner, in the gas sensor 100 of the present embodiment, an electrical change in the oxygen pump cell 135 is transmitted to the oxygen concentration detection cell 150 through the leakage section 148, thereby compensating a delay in change of oxygen concentration in the oxygen concentration detection cell 150. Thus, when the pump current Ip of the oxygen pump cell 135 changes, a linear approach of the output voltage of the oxygen concentration detection cell 150 to the target value is accelerated, thereby restraining the occurrence of the above-mentioned time lag. This also applies to the case where the air-fuel ratio of exhaust gas in the gas detecting chamber 145c is higher than the theoretical air-fuel ratio, and, thus, the oxygen pump cell 135 pumps oxygen out of the gas detecting chamber 145c.

Figure 8:
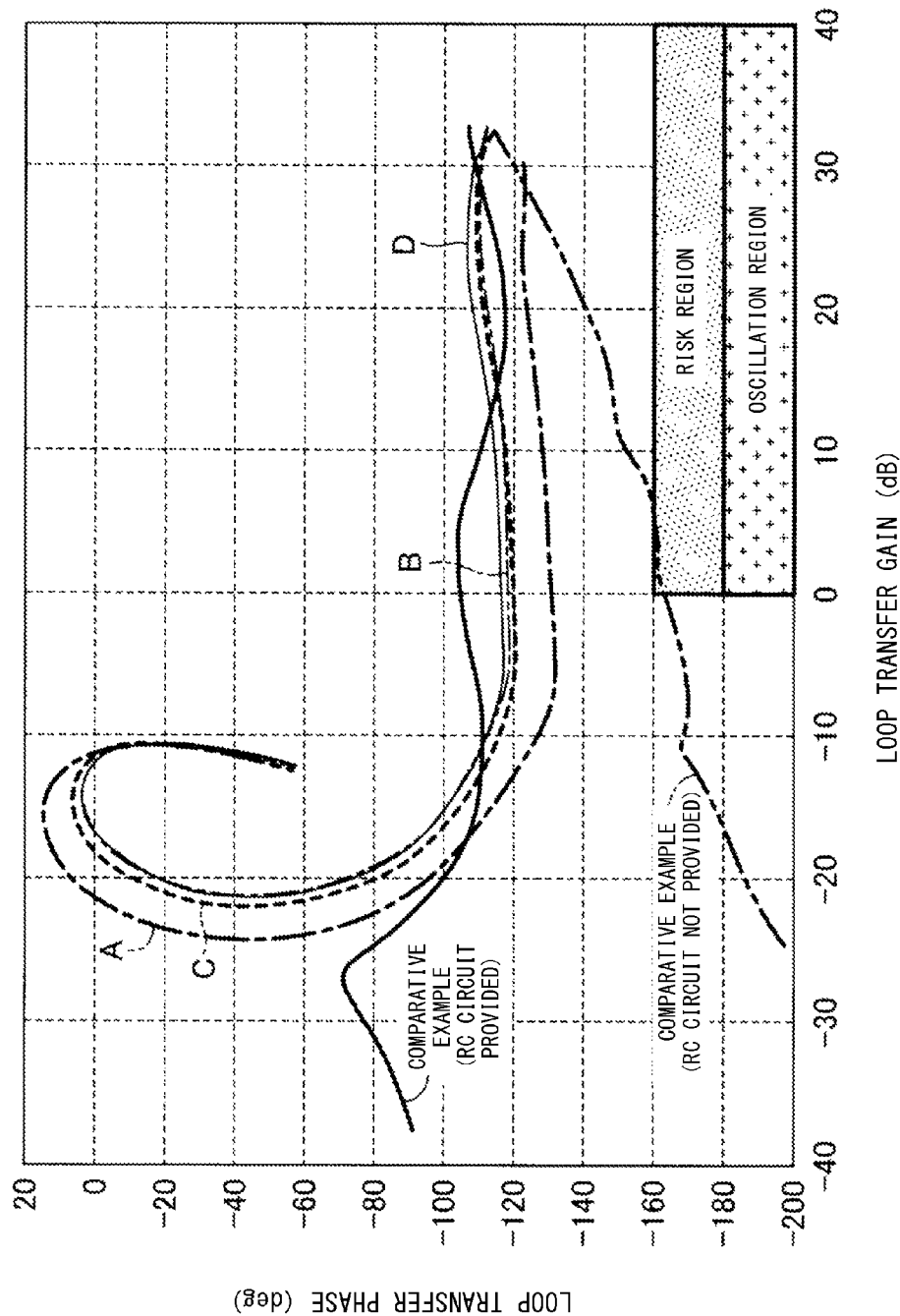
FIG. 8 is an explanatory graph showing the results of experiments on oscillation characteristics with respect to leak-section patterns A to D.

FIG. 8 is an explanatory graph showing the results of experiments on oscillation characteristics with respect to patterns A to D (FIG. 6) of the leakage section 148. The present inventors evaluated the performance of the gas sensor 100 of the present embodiment as follows. The present inventors cyclically applied, as a disturbance, a voltage change in a predetermined range to the oxygen concentration detection cell 150. The inventors measured, as a sensor gain, the ratio of an output voltage $\Delta$Vs of the oxygen concentration detection cell 150 which has changed due to the disturbance, to a pump current $\Delta$Ip which has changed due to the disturbance, and measured, as a sensor phase, a shift of the phase of the output voltage $\Delta$Vs from the phase of the pump current $\Delta$Ip. Furthermore, the inventors measured, as a control circuit gain, the ratio of the pump current $\Delta$Ip output from the control circuit 200 to the output voltage $\Delta$V input to the control circuit 200, and measured, as a control circuit phase, a shift of the phase of the pump current $\Delta$Ip output from the control circuit 200, from the phase of the output voltage $\Delta$Vs input to the control circuit 200. The total of the sensor gain and the control circuit gain was taken as a loop transfer gain, and the total of the sensor phase and the control circuit phase was taken as a loop transfer phase.

In the graph of FIG. 8, the horizontal axis represents the loop transfer gain (dB), and the vertical axis represents the loop transfer phase (deg). The graph also shows oscillation characteristics of comparative examples in addition to the oscillation characteristics of patterns A to D (FIG. 6) of the leakage section 148. The gas sensors of the comparative examples do not have the leakage section. Regarding oscillation characteristics of the comparative examples, the graph shows oscillation characteristics in the case where the control circuit 200 has an RC circuit for restraining oscillation, and oscillation characteristics in the case where the control circuit 200 does not have the RC circuit. In the case of patterns A to D (FIG. 6) of the leakage section 148, the control circuit 200 does not have the RC circuit for restraining oscillation.

Figure 9:
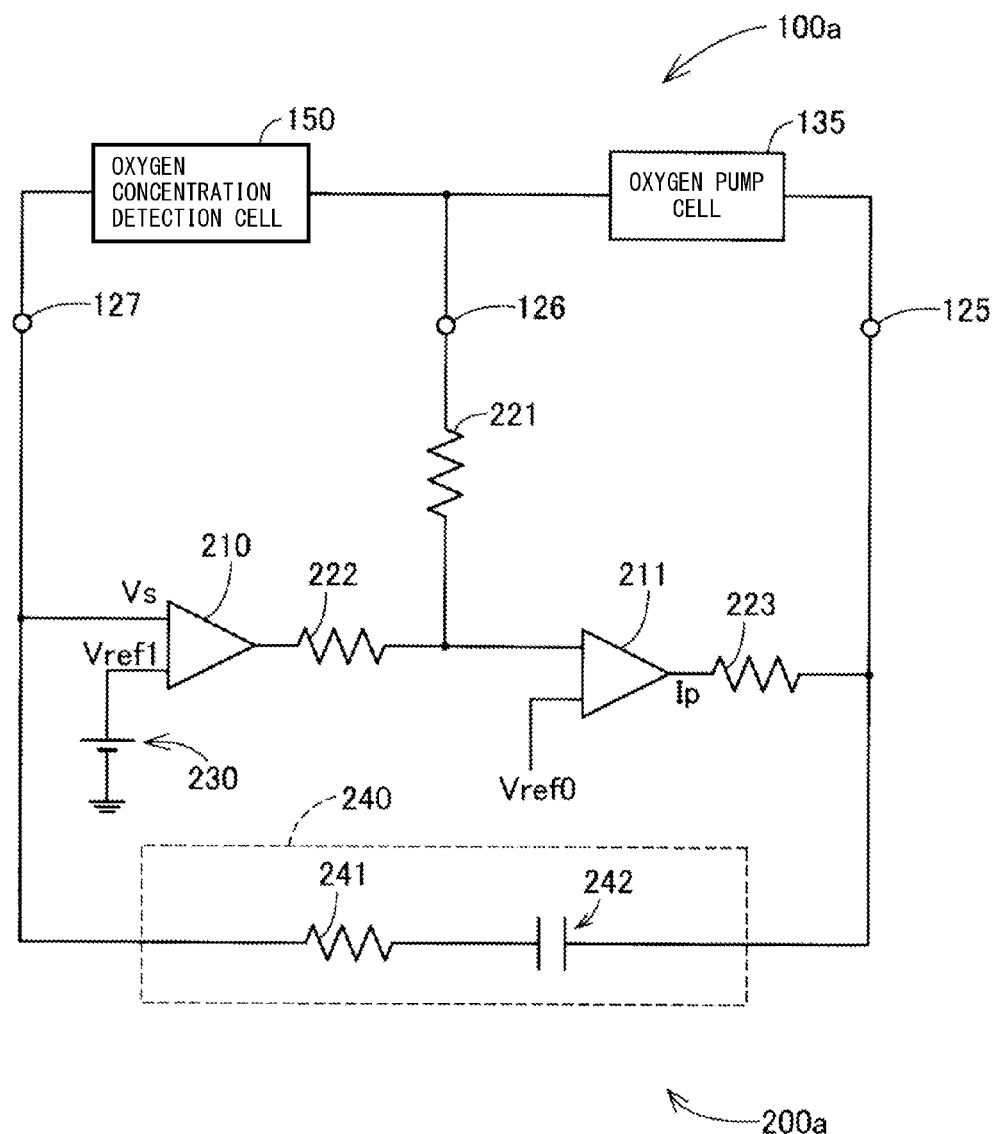
FIG. 9 is a schematic diagram showing an example configuration of the control circuit for a gas sensor of a comparative example.

FIG. 9 is a schematic diagram showing an example configuration of a control circuit 200a connected to a gas sensor 100a of a comparative example. FIG. 9 is substantially similar to FIG. 7 except that the leakage section 148 is not provided, and a high-pass filter 240 is provided for restraining oscillation. The control circuit 200a performs feedback control on the gas sensor 100a similar to the case of the control circuit 200 for use with the gas sensor 100 of the present embodiment. In feedback control, the control circuit 200a restrains the occurrence of oscillation by means of the high-pass filter 240 provided therein.

The high-pass filter 240 is an RC circuit having a resistance 241 and a capacitor 242 connected in series. Connection of the high-pass filter 240 is such that the resistance 241 is connected to the Vs electrode pad 127, whereas the capacitor 242 is connected to the Ip electrode pad 125. When the pump current changes in direction of flow in the oxygen pump cell 135, the high-pass filter 240 allows current to flow therethrough in a predetermined amount. By virtue of current flowing in a predetermined amount through the high-pass filter 240, the control circuit 200a can mitigate a delay in voltage change of the oxygen concentration detection cell 150 in response to a change in the pump current of the oxygen pump cell 135. Therefore, the occurrence of oscillation in the control circuit 200a is restrained.

Referring to the graph of FIG. 8, it is empirically known that there is the risk of oscillation in a region ("risk region" in the graph) where the loop transfer phase is −160° or less at a loop transfer gain of 0 dB or more and that the possibility of oscillation is considerably high in a region ("oscillation region" in the graph) where the loop transfer phase is −180° or less at a loop transfer gain of 0 dB or more. Therefore, preferably, in the graph of FIG. 8, the oscillation characteristics are plotted above these regions.

Regarding the comparative examples having no leakage section, in the case where the RC circuit for restraining oscillation is not provided, the oscillation characteristics are plotted near the risk region, potentially resulting in oscillation of the control circuit 200a. However, in the case of the comparative example in which the RC circuit is provided for restraining oscillation, the oscillation characteristics are shifted considerably above the risk region; therefore, the possibility of oscillation of the control circuit 200a can be reduced.

Meanwhile, regarding patterns A to D (FIG. 6) of the leakage section 148, the oscillation characteristics are plotted considerably above the risk region; thus, it is understandable that the possibility of oscillation of the control circuit 200 is sufficiently low. Among the four patterns A to D, pattern D exhibits the best oscillation characteristics, and pattern A exhibits the poorest oscillation characteristics. As described with reference to FIG. 5D, in pattern D the second leakage section 148d extends rearward beyond the rear ends of the two solid electrolyte bodies 136 and 151. Thus, for the purpose of restraining oscillation, preferably, the leakage section 148 is arranged so as to extend rearward beyond the rear ends of the two solid electrolyte bodies 136 and 151.

As described above, in the present embodiment, since the leakage section 148 is arranged so as to partially constitute the wall of the gas detecting chamber 145c, oscillation of the control circuit 200 can be sufficiently restrained.

Conventionally, exposure of the leakage section 148 to exhaust gas has brought about the following concerns: water contained in exhaust gas adhering to the outer surface of the leakage section 148 causes cracking of the leakage section 148, and carbon adhering to the outer surface of the leakage section 148 causes blackening. Thus, investigators considered it preferable to leave the leakage section 148 unexposed to the gas detecting chamber 145c into which the exhaust gas is introduced. However, experiments conducted by the present inventors have revealed that, even when the leakage section 148 is arranged so as to be exposed to the gas detecting chamber 145c (i.e., so as to partially constitute the wall of the gas detecting chamber 145c), since water and carbon contained in exhaust gas are mostly interrupted by the diffusion controlling portions 146, no practical problem arises. However, preferably, the entire perimetrical surface of the leakage section 148 is covered with the spacer 145. Also, by arranging the leakage section 148 so as to partially constitute the wall of the gas detecting chamber 145c as in the case of the present embodiment, as compared with the case where the leakage section 148 is provided away from the wall of the gas detecting chamber 145c, the two solid electrolyte bodies 136 and 151 can be electrically connected to each other with a lower electrical resistance (i.e., in a condition that is closer to a short circuit), whereby the effect of restraining oscillation can be further enhanced.

Modified Embodiments:

The present invention is not limited to the above-described embodiment, but may be embodied in various other forms without departing from the gist of the invention. For example, the size and the position of formation of the leakage section 148 are not limited to those described in the above embodiment and the example arrangements. The leakage section 148 may be arranged so as to allow for electrical communication between the oxygen pump cell 135 and the oxygen concentration detection cell 150.

Modified Embodiment 1:

In the gas sensor 100 of the above embodiment, the leakage section 148 is provided in a region which overlies the heat-generating resistor 163 of the heater element 160 when the gas sensor element 120 is viewed from the laminating direction. However, the leakage section 148 may be provided externally of the region. Even so, the leakage section 148 is preferably provided in the region, since the temperature of the leakage section 148 can be appropriately controlled. The leakage section 148 may be provided in the vicinity of the heat-generating resistor 163 so as to be heated by the heat-generating resistor 163.

Modified Embodiment 2:

In the above embodiment, the control circuit 200 is configured to combine the PID element 210 and the operational amplifier 211. However, the control circuit 200 may employ a different configuration.

Modified Embodiment 3:

In the above embodiment, the oxygen pump cell 135 is configured such that the paired electrodes 137 and 138 are disposed on respective opposite surfaces of the first solid electrolyte body 136. Further, the oxygen concentration detection cell 150 is configured such that the paired electrodes 152 and 153 are disposed on respective opposite surfaces of the second solid electrolyte body 151. However, the oxygen pump cell 135 may be configured such that the paired electrodes 137 and 138 are disposed on one of the opposite surfaces of the first solid electrolyte body 136, and the oxygen concentration detection cell 150 may be configured such that the paired electrodes 152 and 153 are disposed on one of the opposite surfaces of the second solid electrolyte body 151. Furthermore, in the above embodiment, the paired electrodes 137 and 138 of the oxygen pump cell 135 and the paired electrodes 152 and 153 of the oxygen concentration detection cell 150 are disposed at substantially the same position with respect to the longitudinal direction (a direction along the axial line AX) of the gas sensor element 120. However, the paired electrodes 137 and 138 of the oxygen pump cell 135 and the paired electrodes 152 and 153 of the oxygen concentration detection cell 150 may be disposed at different positions with respect to the longitudinal direction.

Modified Embodiment 4:

In the above embodiment, the gas sensor 100 employs the solid electrolyte bodies 136 and 151 which can conduct oxygen ions, for detecting the concentration of oxygen gas contained in gas to be measured. However, the gas sensor 100 may be adapted to detect the concentration of a gas other than oxygen.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No.2014-011383 filed Jan. 24, 2014, incorporated herein by reference in its entirety.

What is claimed is:

1. A gas sensor element comprising:
   a measuring chamber into which a gas to be measured is introduced;
   an oxygen concentration detection cell which generates an output voltage corresponding to oxygen concentration in the measuring chamber and which comprises a plate-shaped first solid electrolyte body and a first pair of electrodes disposed on the first solid electrolyte body, at least a portion of a first electrode of the first pair of electrodes directly overlaying the measuring chamber;

an oxygen pump cell which comprises a plate-shaped second solid electrolyte body and a second pair of electrodes disposed on the second solid electrolyte body, the oxygen pump cell being laminated on the oxygen concentration detection cell with the measuring chamber intervening therebetween so that at least a portion of a second electrode of the second pair of electrodes faces the measuring chamber, and which oxygen pump cell pumps oxygen into or out of the measuring chamber in accordance with a pump current input thereto such that the output voltage generated by the oxygen concentration detection cell assumes a predetermined target voltage;

an insulating layer formed of an insulating member in which the measuring chamber is formed and which is disposed between the first and second solid electrolyte bodies so as to electrically insulate the oxygen concentration detection cell from the oxygen pump cell; and a leakage section formed primarily of a solid electrolyte material and which electrically connects the oxygen concentration detection cell and the oxygen pump cell, wherein the leakage section is exposed to and faces the measuring chamber and forms a wall of the measuring chamber, wherein the entire perimetrical surface of the leakage section is covered by the insulating layer.

2. The gas sensor element as claimed in claim 1, wherein, when, of opposite sides of the gas sensor element with respect to an axial direction of the gas sensor element, a side where the measuring chamber is provided is defined as a forward side and a side opposite the forward side is defined as a rearward side, the leakage section includes at least one of a first leakage section which forms a wall of the measuring chamber on the forward side, and a second leakage section which forms a wall of the measuring chamber on the rearward side.

3. The gas sensor element as claimed in claim 1, wherein the leakage section extends rearward beyond a rear end of each of the first and second solid electrolyte bodies.

4. The gas sensor element as claimed in claim 2, wherein the leakage section extends rearward beyond a rear end of each of the first and second solid electrolyte bodies.

5. A gas sensor comprising a gas sensor element for detecting a particular gas contained in a gas to be measured, wherein the gas sensor element is the gas sensor element as claimed in claim 1.

6. The gas sensor element as claimed in claim 1, wherein in any section of the leakage section taken perpendicularly to a laminating direction, the insulating layer exists in the same section.

* * * * *